(12) United States Patent
Barbieri et al.

(10) Patent No.: US 8,121,984 B2
(45) Date of Patent: Feb. 21, 2012

(54) METHOD AND SYSTEM FOR ARCHIVING BIOMEDICAL DATA GENERATED BY A DATA COLLECTION DEVICE

(75) Inventors: Robert S. Barbieri, Schnecksville, PA (US); Gregory Robert Glick, Allentown, PA (US); Michael Andrew Magent, Allentown, PA (US); Michael S. Toth, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 504 days.

(21) Appl. No.: 12/284,931

(22) Filed: Sep. 25, 2008

(65) Prior Publication Data

US 2010/0082707 A1    Apr. 1, 2010

(51) Int. Cl.
*G06F 17/00* (2006.01)
(52) U.S. Cl. ............. 707/670; 707/661; 705/2; 713/189
(58) Field of Classification Search .................. None
See application file for complete search history.

(56) References Cited

U.S. PATENT DOCUMENTS

| | | | | |
|---|---|---|---|---|
| 5,664,109 A * | 9/1997 | Johnson et al. | ................... | 705/2 |
| 6,221,011 B1 * | 4/2001 | Bardy | .......................... | 600/300 |
| 6,470,320 B1 | 10/2002 | Hildebrand et al. | | |
| 6,804,787 B2 * | 10/2004 | Dick | ................................. | 726/1 |
| 6,847,933 B1 * | 1/2005 | Hastings | .......................... | 705/2 |
| 7,038,595 B2 * | 5/2006 | Seely | ....................... | 340/870.07 |
| 7,234,064 B2 * | 6/2007 | Menschik et al. | ............ | 713/193 |
| 7,424,437 B2 * | 9/2008 | Maus et al. | ....................... | 705/2 |
| 7,464,043 B1 * | 12/2008 | Dussia | ............................. | 705/3 |
| 7,529,685 B2 * | 5/2009 | Davies et al. | ..................... | 705/3 |
| 7,668,835 B2 * | 2/2010 | Judd et al. | ................ | 707/999.01 |
| 2002/0099686 A1 | 7/2002 | Schwartz et al. | | |
| 2002/0111833 A1 * | 8/2002 | Dick | ................................ | 705/3 |
| 2002/0116227 A1 * | 8/2002 | Dick | ................................ | 705/3 |
| 2003/0101076 A1 | 5/2003 | Zaleski | | |
| 2003/0215092 A1 * | 11/2003 | Dick | ............................... | 380/246 |
| 2003/0217290 A1 * | 11/2003 | Dick | ............................... | 713/201 |
| 2004/0143594 A1 * | 7/2004 | Kalies | ....................... | 707/103 R |
| 2004/0193901 A1 * | 9/2004 | Bharara | ......................... | 713/193 |
| 2005/0114334 A1 * | 5/2005 | Ober et al. | ....................... | 707/9 |
| 2005/0165623 A1 * | 7/2005 | Landi et al. | ....................... | 705/2 |
| 2005/0236474 A1 * | 10/2005 | Onuma et al. | ................. | 235/382 |
| 2006/0026156 A1 * | 2/2006 | Zuleba | .............................. | 707/5 |
| 2006/0266826 A1 * | 11/2006 | Banfield et al. | ............... | 235/383 |

* cited by examiner

*Primary Examiner* — Hung Le
(74) *Attorney, Agent, or Firm* — Willard Jones, II (57) ABSTRACT

A method for archiving biomedical data generated by a data collection device, includes the steps of automatically determining a data format in which the collection device is configured to store the biomedical data onto a computer-readable storage medium, based on the data format, extracting the biomedical data from the storage medium, and transmitting the extracted data to a database in which the extracted data is archived.

17 Claims, 5 Drawing Sheets

METHOD AND SYSTEM FOR ARCHIVING BIOMEDICAL DATA GENERATED BY A DATA COLLECTION DEVICE

BACKGROUND OF THE INVENTION

This invention relates to a method and a system for archiving biomedical data generated by a data collection device.

Biomedical data generated by data collection devices that collect data from patients provide an important source of information for medical research. However, collection of data for research is a secondary objective, whereas collection of data for treating the patient has always been a primary concern for physicians. In general, physicians are only interested in a subset of the data generated by a manufacturer-specific, e.g., proprietary, collection device. This subset may include only those data which relate to treatment and diagnosis of the patient. For example, if the collection device is a pacemaker, the pacemaker may be periodically monitored to ensure continued operability.

Although the subset of data may be sufficient for the physician's purposes, it may be desirable to collect additional data which may be of interest to researchers. Many data collection devices are by default, configured to collect a large amount of data that exceeds the data subset used by physicians. The amount of information that collection devices are capable of generating will only increase as technology advances. Currently, this additional information is not being utilized. Moreover, obtaining access to the additional information has not been possible because manufacturers have failed to provide the collection devices with the capability of utilizing the additional data. Often, the additional data is discarded after the data subset is recorded. Other times, the collection devices may save all of the data to a floppy disk, but even then the data is saved using a proprietary data format which only the collection device can recognize and, as stated above, the collection devices have not been provided with the capability of using the additional data.

Accordingly a need exists for techniques which enable the additional data to be put to practical use.

DETAILED DESCRIPTION OF THE INVENTION

According to a first aspect of the present invention, there is provided a method for archiving biomedical data generated by a data collection device, comprising: automatically determining a data format in which the collection device is configured to store the biomedical data onto a computer-readable storage medium; based on the data format, extracting the biomedical data from the storage medium; and transmitting the extracted data to a database in which the extracted data is archived.

According to a second aspect of the present invention, there is provided a data extraction device for archiving biomedical data generated by a data collection device, the extraction device being constructed and arranged to: automatically determine a data format in which the collection device is configured to store the biomedical data onto a computer-readable storage medium; based on the data format, extract the biomedical data from the storage medium; and transmit the extracted data to a data processing device configured to transmit the extracted data to a database in which the extracted data is archived.

According to a third aspect of the present invention, there is provided a system for archiving biomedical data, comprising: a data collection device configured to collect and store biomedical data onto a computer-readable storage medium; a data extraction device configured to: determine a data format in which the biomedical data is stored, and based on the data format, extract the biomedical data from the storage medium; and a data processing device configured to: receive the extracted data, remove any identifying information associated with an individual from whom the extracted data was collected, to generate a de-identified data record, and transmit the de-identified data record to a database in which the data record is archived.

According to a fourth aspect of the present invention, there is provided a computer-readable medium having stored thereon a series of instructions executable by a processor for archiving biomedical data generated by a data collection device, the instructions configured to cause the processor to perform the steps of: automatically determining a data format in which the collection device is configured to store the biomedical data onto a computer-readable storage medium; based on the data format, extracting the biomedical data from the storage medium; and transmitting the extracted data for archiving in a database.

Examples

Exemplary embodiments of the present invention will be described with reference to the archiving of biomedical data generated by a data collection device. In particular, the example embodiments relate to the archiving of electrocardio data. However, it will be appreciated that the exemplary embodiments of the present invention described below may be adapted towards the archiving of any type of data generated by a collection device. The exemplary embodiments may be utilized in conjunction with other systems and methods for archiving or sharing data. In particular, the exemplary embodiments may be compatible with, e.g., medical research systems in which access to patient data is provided to a plurality of researchers.

Figure 1:
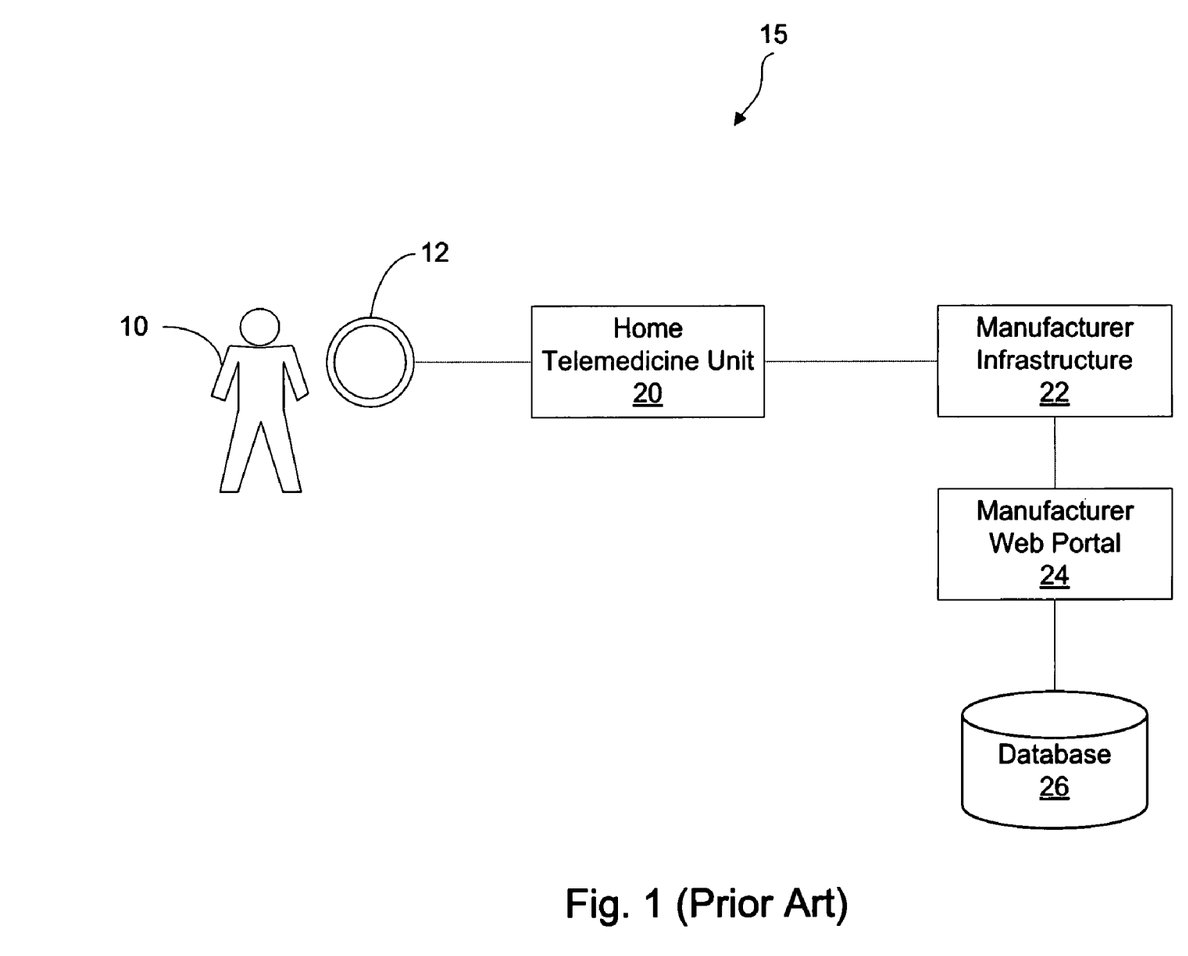
FIG. 1 shows a conventional data collection system.

FIG. 1 shows a conventional data collection system 15 which may include components for data collection at a patient's home. The system 15 may include a sensor arrangement 12, a home telemedicine unit 20, a manufacturer infrastructure 22, a manufacturer web portal and a database 26. In the system 15, a patient 10 may be a cardiac patient with an implanted cardioverter-defibrillator (ICD), a cardiac resynchronization therapy device (CRT) such as pacemaker, or any other collection device.

The sensor arrangement 12 may be an interrogation wand in communication with the pacemaker and the telemedicine unit 20. Electromagnetic signals emitted by the pacemaker are sensed by the sensor arrangement 12 and transmitted to the telemedicine unit 20.

The telemedicine unit 20 may be a manufacturer-supplied unit configured to generate data corresponding to the signals sensed by the sensor arrangement 12. The telemedicine unit 20 may be proprietary. In particular, the telemedicine unit 20 may only be compatible with a particular model of pacemaker, e.g., a manufacturer-branded pacemaker. The telemedicine unit may be configured to record only a limited set of data needed for treating the patient 10.

The infrastructure 22 may include both proprietary and non-proprietary components, such as a telephone line or an Internet connection coupled to the telemedicine unit 20. The infrastructure may also include a data collection device configured to collect the signals transmitted by the sensor arrangement 12 and to transmit the signals to the database 26 via the web portal 24.

The database 26 may be a patient database controlled by a manufacturer or a third-party testing facility for storing patient data, e.g., test results. Data contained in the database 26 may be used to generate reports at the request of physicians.

Figure 2:
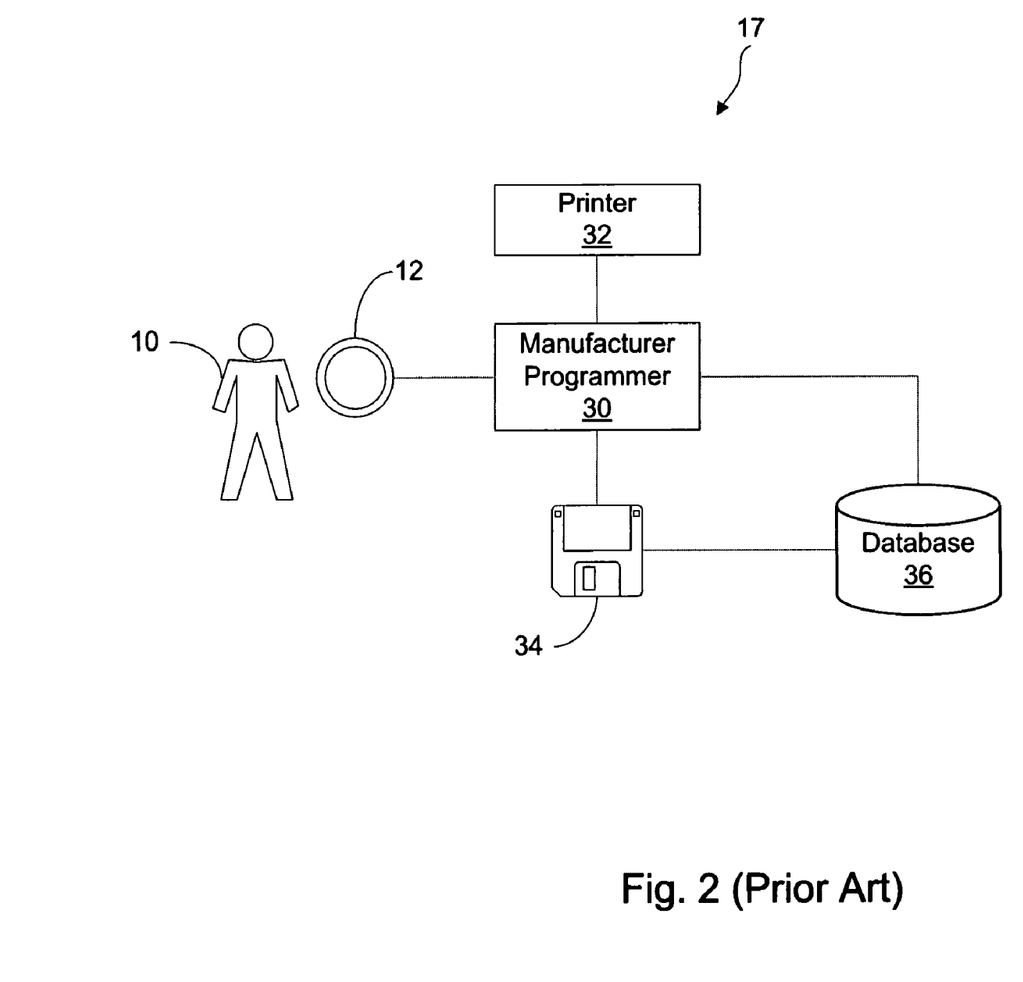
FIG. 2 shows another conventional data collection system.

FIG. 2 shows a conventional data collection system 17 which may include the patient 10, the sensor arrangement 12, a manufacturer programmer 30, a printer 32, a floppy disk 34 and a database 36. The system 17 may be located in a physician's office in which the programmer 30 is used to generate data for any number of patients treated.

The programmer 30 is a manufacturer-specific device configured to generate data corresponding to the signals sensed by the sensor arrangement 12. As such, the programmer 30 is designed to store the generated data in a proprietary data format. The programmer 30 may be configured to transmit a subset of the generated data to the database 36. Alternatively, the programmer 30 may be configured to generate a printed report via the printer 32. The printed report and the data subset transmitted to the database 36 may be limited to only that information which is necessary for treating the patient. In particular, the data subset may include basic device information, e.g., battery life, electrocardiogram (ECG or EKG) signals, and various trace signals of clinical interest. The programmer may also be configured to store more than a subset of the generated data, e.g., all of the generated data, onto the floppy disk 34 using a proprietary data format.

The database 36 may be a patient database used by the physician for storing patient records.

Figure 3:
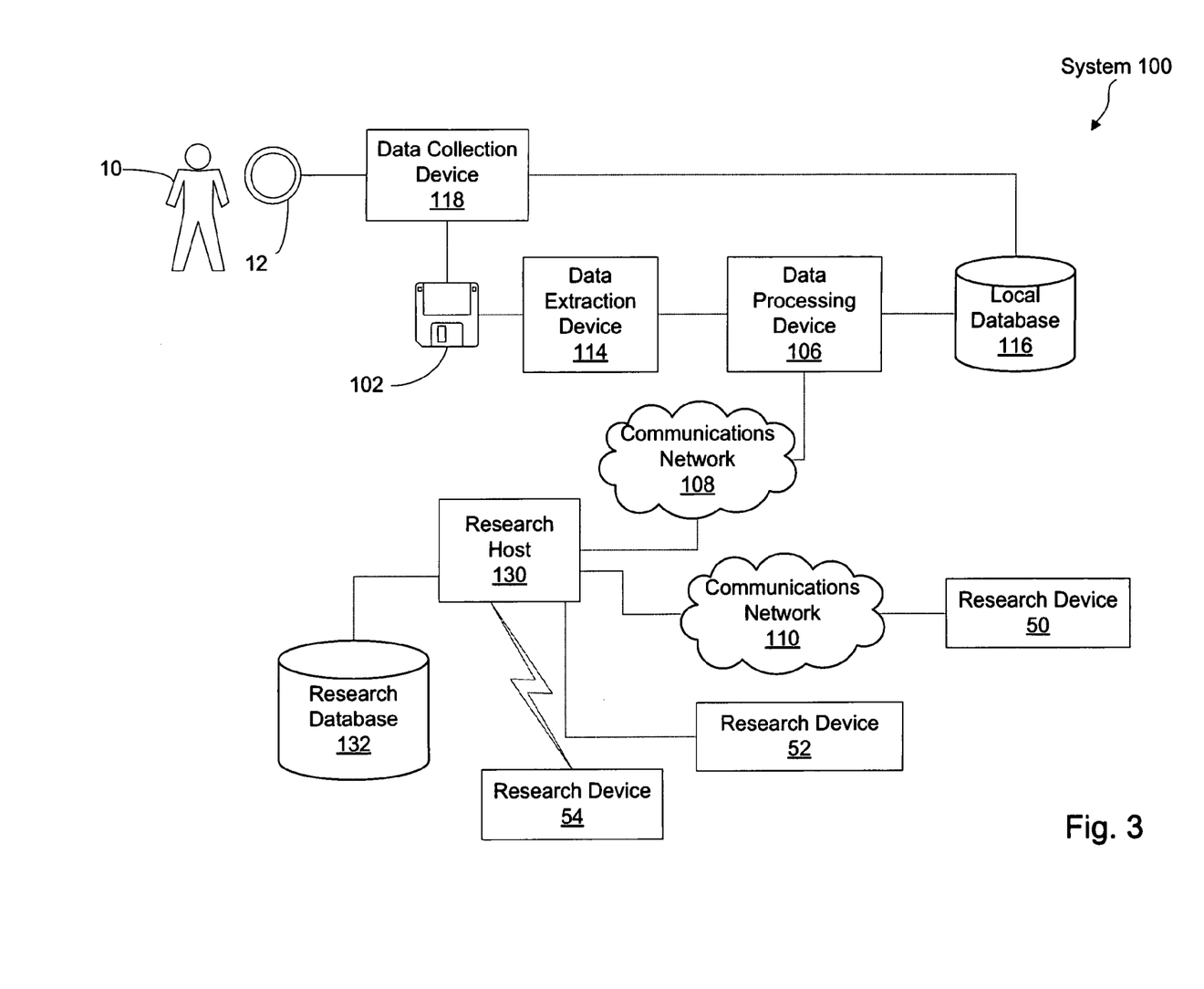
FIG. 3 shows an example of a system for archiving biomedical data generated by a data collection device according to an example embodiment of the present invention.

FIG. 3 shows an example of a system 100 for archiving biomedical data generated by a data collection device according to an example embodiment of the present invention. The system 100 may include the patient 10, the sensor arrangement 12, a data collection device 118, a portable computer-readable storage medium 102, a data extraction device 114, a data processing device 106, a local database 116, a research host 130, a research database 132, one or more research devices 50, 52 and 54, and communications networks 108 and 110.

The collection device 118 may be a manufacturer-specific device which is default-configured to transmit a subset of the data it collects to the database 116. A remaining portion of the collected data may be stored, along with the data subset itself, onto the storage medium 102 using a proprietary data format. Examples of data generated by the collection device 118 include, but may not be limited to, statistical data, e.g., relating to the patient 10 or the pacemaker, device information for the pacemaker or the collection device 118, and recordings of abnormal clinical events, e.g., abnormal heart rhythms such as tachycardia and fibrillation in an atria or a ventricle. Similar to the programmer 30, the collection device 118 may be located at a physician's office and may be used to collect patient data when the patient 10 visits the office for treatment.

The storage medium 102 may be a floppy disk or any other computer-readable medium. Preferably, the storage medium 102 is a portable medium such as a flash drive, a CD, a DVD, or a removable memory. Alternatively, the storage medium 102 may be non-removable, e.g., part of a system memory of the collection device 118. The storage medium 102 may contain, in addition to the data subset, additional data of interest to researchers such as statistical data, device information, e.g., detailed device parameters, and abnormal clinical events. The additional data may be stored in a proprietary format. For example, the format may be a manufacturer-specific binary file format in which the additional data may be stored, together with other data such as the data subset, according to a predetermined file structure. Data formats may vary across manufacturers and a collection device compatible with a implanted device from one manufacturer may not be compatible with implanted devices from other manufacturers or even other implanted devices from the same manufacturer.

The processing device 106 may be a general purpose computing device, e.g., a laptop, a personal computer, a server, etc. The processing device 106 may alternatively be a specialized device dedicated to collecting patient data and transmitting the data to the database 116. For example, the processing device 106 may include an application-specific integrated circuit (ASIC), a microcontroller, or other hardware arrangement configured to receive data from the extraction device. The processing device 106 may be configured to transmit the data subset to, and retrieve the data subset from, the database 116. Optionally, the processing device 106 may be configured to transmit the data subset to the research host 130. The processing device 106 may also be configured to transmit the additional data to the research host 130, but not to the database 116.

The database 116 may be a patient database used by the physician for storing patient records and may include data from patients whose information may be shared with others, e.g., participants in a research project. The database 116 may also include data from patients whose information is private and used only by the physician and/or a physician affiliate. The database 116 may be located in a memory of the processing device 106, or on a separate device such as an office server or a remote server.

The extraction device 114 may be a peripheral device in communication with the processing device 106 and the storage medium 102. In one embodiment, the extraction device 114 may be implemented as a portable universal reader device configured to extract the additional data from the storage medium 102. The extraction of the additional data will be described in further detail below. In another embodiment, the extraction device 114 may be integral with the processing device 106, e.g., provided as a hardware or software module.

The communications networks 108 and 110 may be any type of wired or wireless network including, for example, a virtual private network, a local area network, a wide area network, the Internet, etc. The communications networks 108 and 110 may also include any number of sub-networks. The communications networks 108 and 110 may be configured to allow data communication between various system components.

For example, the communications network 110 may communicatively couple the research host 130 and the research device 50. It may also be possible to communicate directly with the research host 130. For example, the research device 52 may be in wired communication with the research host 130 while the device 54 may be in wireless communication with the research host 130, e.g., via a direct IEEE 802.1x connection or indirectly through a wireless provider.

The research host 130 may be a research facility or a third-party research coordinator in communication with a plurality of data sources, such as hospitals, academic institutions, clinics, private physicians and researchers. The research host 130 may provide the infrastructure necessary to aggregate and analyze patient data, e.g., data received from the processing device 106 via the communications network 108. The research host 130 may provide the research database 132 as a tool for sharing patient data. The research host 130 may also provide a common platform across which researchers can collaborate with one another, e.g., discussion forums, data simulators, social networking tools, etc.

The research database 132 may reside on a server running a database application, e.g., a relational database application such as Oracle or SQL Server. The research database 132 may archive any number of medical records received from the data sources discussed above.

The research devices 50 to 54 may be any computing device capable of communicating with the research host 130. The research devices 50 to 54 may be configured to transmit requests for patient data records, e.g., the data subset or the additional data. The requests may specify a research identifier as a parameter, e.g., downloading an individual patient's data records. The requests may also be general requests for a plurality of patient data records. In addition, the requests may specify search parameters for obtaining data records that fit specified criteria, e.g., age, medical condition, treatment type, etc.

Figure 4:
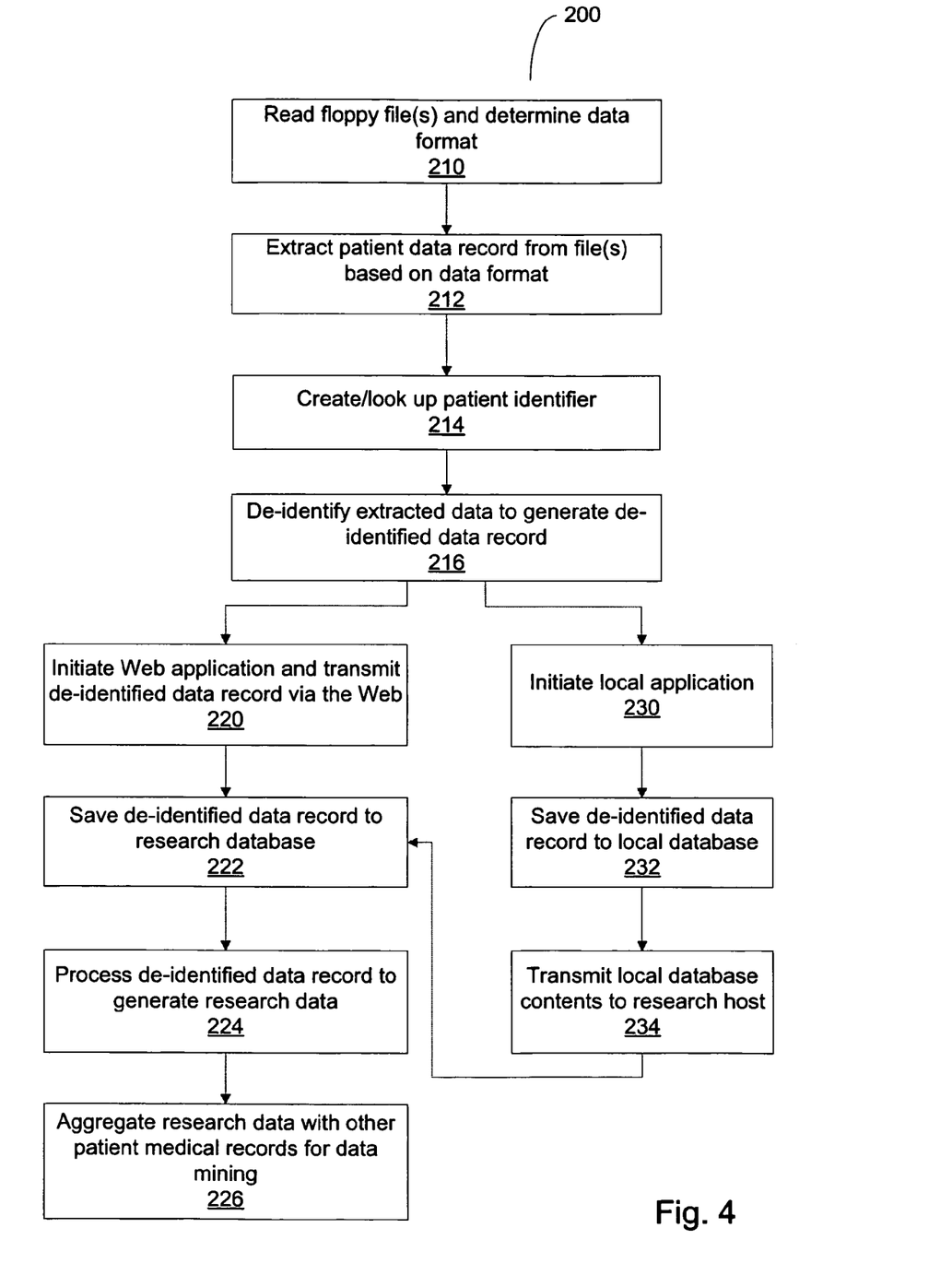
FIG. 4 shows an example of a method for archiving biomedical data generated by a data collection device according to an example embodiment of the present invention.

FIG. 4 shows an example of a method 200 for archiving biomedical data generated by a data collection device according to an example embodiment of the present invention. The method 200 may be implemented in any combination of hardware and/or software, and in particular, using the system 100 described above. However, the method 200 may also be successfully implemented on other systems.

In 210, a floppy disk, e.g., the storage medium 102, may be read and a data format of the data contained therein may be determined. The reading and the data format determination may be performed at the extraction device 114, which may be configured to determine the data format by analyzing a structure or a content of the data. In one embodiment, the extraction device 114 may recognize data formats associated with any number of different manufacturers. Recognition capability may be hard-wired, e.g., on an ASIC or other electric circuit, or on a memory. Alternatively, recognition capability may be soft-coded, e.g., as a software module of a software application or operating system of the extraction device 114.

The content may indicate a manufacturer or a model number of the collection device. The data format may then be determined as a function of the manufacturer and/or the model number. Alternatively, recognition may be based on structure. For example, the extraction device 114 may search the data for data structures that correspond to known formats. If the data appears to be stored in accordance with a known format, then that format may be used to read the data. Another alternative may be based on a trial-and-error approach in which specific portions of the data are analyzed to determine whether the portions could potentially correspond to biomedical data and if so, what type of data, e.g., EKG data, abnormal conditions, etc. The data format determination may be performed automatically. That is, once a physician or other user initiates the determination, no further user input may be required.

In 212, a patient data record including the subset data and/or the additional data may be extracted in accordance with the data format from any files contained on the floppy. Relevant portions of the file(s), as designated by the data format, may be read to obtain the patient data record. The extracted data may be stored, either temporarily or permanently, at the database 116.

In 214, a patient identifier may be created to allow for later cross-matching of the patient data record back to the patient 10. The patient identifier may, for example, be randomly generated. If patient 10 already has a patient identifier, e.g., from previous data collection sessions, then the patient identifier may be looked up, e.g., from the database 116, rather than created. The creation/look up of the patient identifier may be performed at the processing device 106.

In 216, the extracted data may be de-identified to generate a de-identified data record. De-identification may involve the removal of any information which could reveal the identity of the patient 10, including a name, social security number, date of birth, driver's license number, etc.

After 216, the method 200 may proceed to either of 220 or 230, depending on a manner in which the user wishes to transmit the de-identified data record to the research host 130. One option may be to transmit using a remote application, such as a Web application, so as to minimize a need for infrastructure at the physician's office. Accordingly, in 220, a Web application, e.g., a Java applet or a CGI script, may be initiated by the user. The Web application may contact a web server or other Web based computing device located at the research host 130 and configured to receive the de-identified data record via the Web. The method then proceeds to 222.

Another option may be to transmit using a local client application installed at the physician's office, e.g., as a software application on the processing device 106. Accordingly, in 230, the local application may be initiated by the user.

In 232, the de-identified data record may be saved to a local database, e.g., the database 116 before proceeding to 234.

In 234, contents of the local database, e.g., the de-identified data record, may be transmitted to the research host 130. The method then proceeds to 222.

In 222, the de-identified data record may be saved to the research database 132 after transmission via the Web application or the client application.

In 224, the de-identified data record may be processed to generate research data. The research data may include any information which may be of potential interest to researchers. Depending on the nature of a research project, the research data may include any number of information types including, for example, statistical data, abnormal heart events and device information. The research data may be obtained directly from the de-identified data record, or generated through additional data processing, e.g., converting raw data values into human or machine-readable format, performing data analysis, and removing data anomalies.

In 226, the research data may be aggregated with other patient medical records. In particular, the research data may be archived together with the other patient medical records. If the research database 132 includes another record from the patient 10, the other record may be cross-referenced to the research data by associating the patient identifier from 214 with both the other record and the research data. In this manner, the two sources of data may later be cross-matched to the patient 10.

Figure 5:
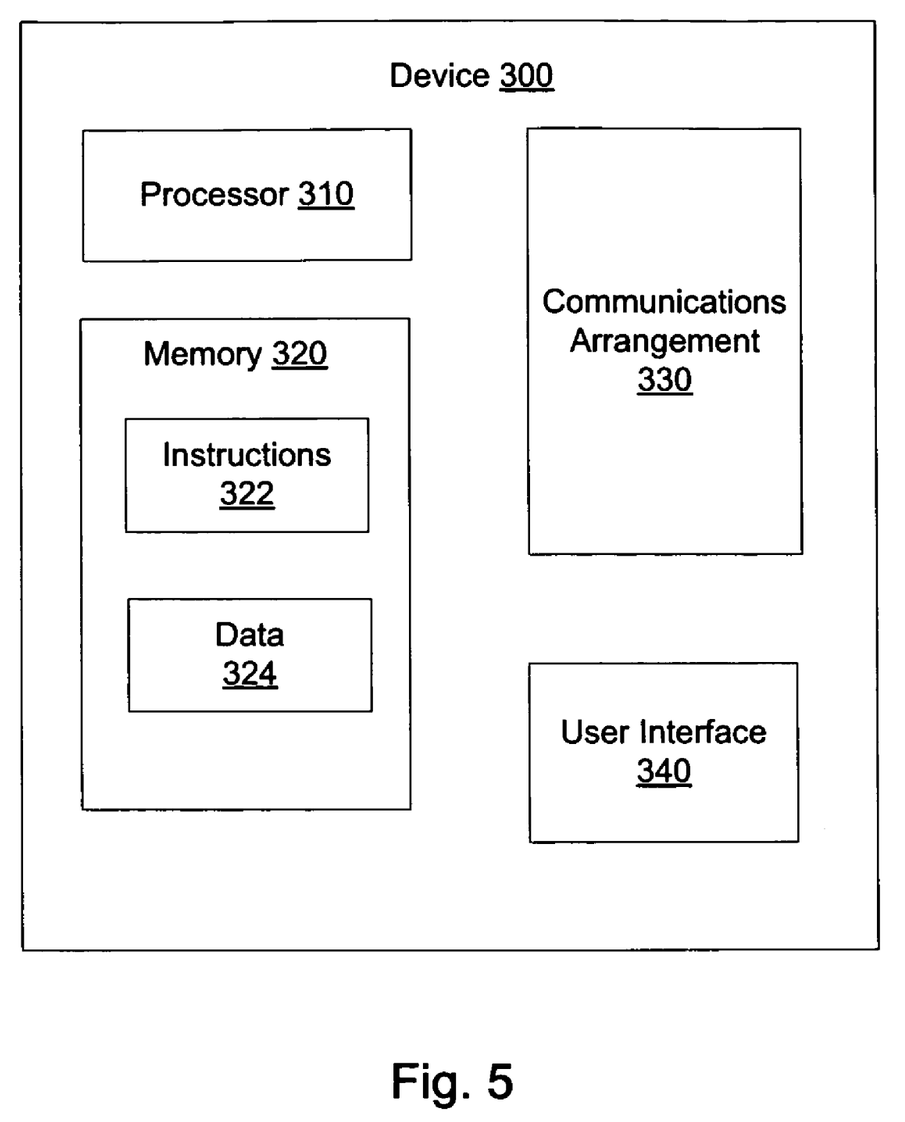
FIG. 5 shows an example of a device for archiving biomedical data generated by a data collection device according to an example embodiment of the present invention.

FIG. 5 shows an example of a device 300 for archiving biomedical data generated by a data collection device according to an example embodiment of the present invention. As discussed above, functions of the extraction device 114 and the processing device 106 may be combined into a single device. The functions may be realized on a computing device such as the device 300, which may include a processor 310, a memory 320, a communications arrangement 330, and a user interface 340.

The communications arrangement 330 may include any hardware and/or software necessary for transmitting and receiving data. The communications arrangement 330 may be configured to communicate with the research host 130 and the database 116, as well as to read data from the floppy 102. Accordingly, the communications arrangement 330 may include a floppy disk reader and a network interface such as an Ethernet card.

The processor 310 may be a microprocessor, an ASIC, or any other electric circuit or combination of circuits configured to perform instructions 322 located in the memory 320.

The memory 320 may include a computer-readable medium which includes the instructions 322 and data 324. The instructions may include, for example, instructions configured to cause the processor 310 to perform one or more steps of the method 200 discussed above. The data 324 may include a temporary storage space for data used in performing the method 200, including the extracted data, the de-identified data record and the patient identifier.

The user interface 340 may include hardware for entering user input. The hardware may, for example, include a keyboard, a display, a keypad, or a touchpad.

In the preceding specification, the present invention has been described with reference to specific example embodiments thereof. It will, however, be evident that various modifications and changes may be made thereunto without departing from the broader spirit and scope of the present invention as set forth in the claims that follow. The specification and drawings are accordingly to be regarded in an illustrative rather than restrictive sense.

The invention claimed is:

1. A method for archiving biomedical data generated by a data collection device, comprising:
   at a computer, reading a file containing the biomedical data from a computer-readable storage medium, wherein a data format of the file, as stored on the storage medium, has not been identified to the computer;
   at a processor of the computer, analyzing the file to determine the data format of the file, wherein the analyzing includes obtaining, from the file, at least one of a manufacturer of the collection device and a model number of the collection device and determining the data format as a function of the at least one of a manufacturer of the collection device and a model number of the collection device;
   based on the data format, locating and extracting the biomedical data from within the file;
   prior to transmitting, removing any identifying information associated with an individual from whom the biomedical data was collected; and
   transmitting the extracted data to a database in which the extracted data is archived.

2. The method of claim 1, wherein the at least one of a manufacturer of the collection device and a model number of the collection device is obtained from a content of the biomedical data, as stored on the storage medium.

3. The method of claim 1, further comprising:
   archiving the extracted data together with an additional data record associated with the same individual.

4. The method of claim 3, further comprising:
   associating the extracted data with the additional data record by assigning a research identifier to the extracted data, resulting in a sharing of the research identifier by the extracted data and the additional data record.

5. The method of claim 1, further comprising:
   transmitting the extracted data to the database via one of a local client application and a Web application.

6. The method of claim 1, wherein the biomedical data includes one of statistical data, device information and abnormal clinical events.

7. The method of claim 6, wherein the biomedical data includes electrocardio data and the clinical events are one of atrial events and ventricular events.

8. A data extraction device for archiving biomedical data generated by a data collection device, the extraction device being constructed and arranged to:
   read a file containing the biomedical data from a computer-readable storage medium, wherein a data format of the file, as stored on the storage medium, has not been identified to the extraction device;
   analyze the file to determine a data format of the file, wherein the extraction device performs the analyzing by obtaining, from the file, at least one of a manufacturer of the collection device and a model number of the collection device and determining the data format as a function of the at least one of a manufacturer of the collection device and a model number of the collection device;
   based on the data format, locate and extract the biomedical data from within the file;
   prior to transmission, remove any identifying information associated with an individual from whom the biomedical data was collected; and
   transmit the extracted data to a data processing device configured to transmit the extracted data to a database in which the extracted data is archived.

9. The extraction device of claim 8, wherein the extraction device is configured to obtain the at least one of a manufacturer of the collection device and a model number of the collection device from a content of the biomedical data, as stored on the storage medium.

10. The extraction device of claim 8, wherein the extracted data is archived together with an additional data record associated with the same individual.

11. The extraction device of claim 10, wherein the extracted data is associated with the additional data record by assigning a research identifier to the extracted data, resulting in a sharing of the research identifier by the extracted data and the additional data record.

12. The extraction device of claim 8, wherein the extracted data is transmitted to the database via one of a local client application and a Web application.

13. The extraction device of claim 8, wherein the biomedical data includes one of statistical data, device information and abnormal clinical events.

14. The extraction device of claim 13, wherein the biomedical data includes electrocardio data and the clinical events are one of atrial events and ventricular events.

15. A system for archiving biomedical data, comprising:
   a data collection device configured to collect and store biomedical data onto a computer-readable storage medium in the form of a file having a predetermined data format;
   a data extraction device configured to:
      read the file from the computer-readable storage medium, wherein the data format of the file has not been identified to the extraction device;
      analyze the file to determine the data format of the file, wherein the extraction device performs the analyzing by obtaining, from the file, at least one of a manufacturer of the collection device and a model number of the collection device and determining the data format as a function of the at least one of a manufacturer of the collection device and a model number of the collection device; and based on the data format, locate and extract the biomedical data from within the file; and a data processing device configured to:

receive the extracted data, remove any identifying information associated with an individual from whom the extracted data was collected, to generate a de-identified data record, and transmit the de-identified data record to a database in which the data record is archived.

16. A computer-readable medium having stored thereon a series of instructions executable by a processor of a computer for archiving biomedical data generated by a data collection device, the instructions configured to cause the processor to perform the steps of:

reading a file containing the biomedical data from a computer-readable storage medium, wherein a data format of the file, as stored on the storage medium, has not been identified to the computer;

at the processor, analyzing the file to determine the data format of the file, wherein the analyzing includes obtaining, from the file, at least one of a manufacturer of the collection device and a model number of the collection device and determining the data format as a function of the at least one of a manufacturer of the collection device and a model number of the collection device;

based on the data format, locating and extracting the biomedical data from within the file;

prior to transmitting, removing any identifying information associated with an individual from whom the biomedical data was collected; and transmitting the extracted data for archiving in a database.

17. The method of claim 1, wherein the file is a binary file having a data format specific to a manufacturer of the data collection device.

* * * * *